United States Patent
Bouthillier et al.

(10) Patent No.: US 8,632,531 B2
(45) Date of Patent: *Jan. 21, 2014

(54) INDIRECT FLUID FLOW MEASUREMENT

(75) Inventors: Robert J. Bouthillier, Lincoln, RI (US);
Curtis Jarva, Norwell, MA (US);
Stephen S. Keaney, Groton, MA (US);
Boris Shapeton, Westwood, MA (US);
Jorah Wyer, Providence, RI (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/408,674

(22) Filed: Feb. 29, 2012
(Under 37 CFR 1.47)

(65) Prior Publication Data
US 2012/0165805 A1  Jun. 28, 2012

Related U.S. Application Data

(63) Continuation of application No. 12/342,494, filed on Dec. 23, 2008, now Pat. No. 8,147,443.

(60) Provisional application No. 61/017,426, filed on Dec. 28, 2007.

(51) Int. Cl.
*A61B 18/04* (2006.01)
*A61M 1/00* (2006.01)

(52) U.S. Cl.
USPC ............ 606/31; 606/27; 604/28; 604/31

(58) Field of Classification Search
USPC .................. 604/28–37; 606/27–35, 38
See application file for complete search history.

(56) References Cited

U.S. PATENT DOCUMENTS

| | | | | |
|---|---|---|---|---|
| 5,456,682 | A | * 10/1995 | Edwards et al. | 606/31 |
| 2002/0058933 | A1 | * 5/2002 | Christopherson et al. | 606/34 |
| 2006/0122590 | A1 | * 6/2006 | Bliweis et al. | 606/24 |

* cited by examiner

*Primary Examiner* — Nicholas Lucchesi
*Assistant Examiner* — Leah Stohr
(74) *Attorney, Agent, or Firm* — Fay Kaplun & Marcin, LLP

(57) ABSTRACT

A system is for thermal ablation and includes (a) a heating element heating an ablation fluid flowing through an ablation device and to a target region of a body and (b) a computing arrangement controlling power supplied to the heating element supplying power to heat the ablation fluid to a desired temperature. The computing arrangement reduces the supplied power when a detected ablation fluid temperature exceeds a desired temperature and increases the supplied power when the detected ablation fluid temperature is below the desired temperature. The computing arrangement monitors a percentage of heat supplied by the heating arrangement to heat the fluid to the desired temperature as a function of a maximum amount of heat which the heating element is capable of supplying.

19 Claims, 2 Drawing Sheets

INDIRECT FLUID FLOW MEASUREMENT

PRIORITY CLAIM

This application is a Continuation application of U.S. patent application Ser. No. 12/342,494 filed on Dec. 23, 2008, now U.S. Pat. No. 8,147,443; which claims the priority to the U.S. Provisional Application Ser. No. 61/017,426, entitled "Indirect Fluid Flow Measurement" filed on Dec. 28, 2007. The specification of the above-identified patent/application is incorporated herewith by reference.

FIELD OF THE INVENTION

The present invention relates to systems and methods for determining a rate of fluid flow through an ablation device.

BACKGROUND

One technique for the treatment of menorrhagia relates to the ablation of uterine lining using heated fluid which is withdrawn via a return lumen. Such systems are heavily reliant on the maintenance of substantially constant circulating fluid level and flow rate within the uterus to ensure the safety, efficiency and effectiveness of the treatment. Undesirable circulating fluid levels and flow rates may prevent the heated fluid from reaching and properly ablating the entire surface area of the lining of the uterus.

SUMMARY OF THE INVENTION

The present invention is directed to a method for ablating tissue comprising controlling a heating element using a variable phase angle control to heat an ablation fluid to a desired temperature and determining a heating percentage corresponding to a percentage of a maximum available heating power represented by a current level of power supplied to the heating element and, when the heating percentage remains below a threshold level for a predetermined period of time, indicating a flow obstruction condition of the fluid.

The present invention is further directed to a system for thermal ablation comprising a heating element for heating an ablation fluid and a computing arrangement controlling power supplied to the heating element based on a proportional, integral and derivative (PID) algorithm, the computing arrangement monitoring power required by the heating element to sustain a desired temperature of the ablation fluid and executing a safety procedure when the power supplied to the heating element over a predetermined period of time drops below a threshold level.

BRIEF DESCRIPTION OF THE DRAWINGS

The accompanying drawings, which are incorporated in and constitute a part of this specification, illustrate several embodiments of the invention and, together with the description, serve to explain the principles of the invention. In the drawings.

DETAILED DESCRIPTION

Figure 1:
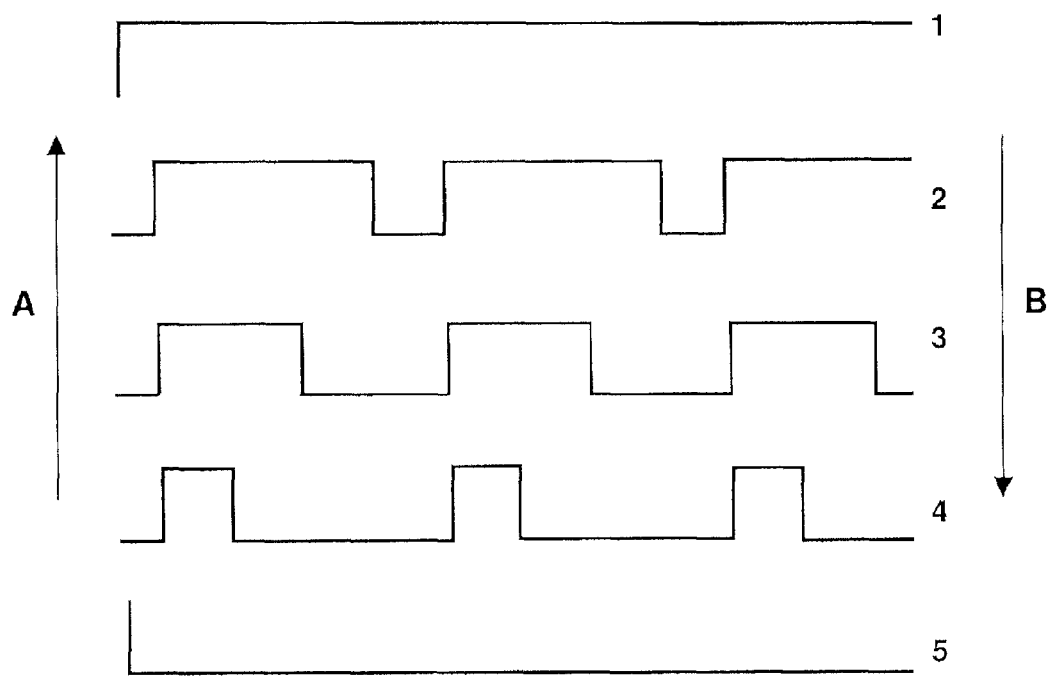
FIG. 1 shows a pulse width modulated signal according to exemplary embodiments of the present invention.

The present invention may be further understood with reference to the following description. The present invention relates to a system and method for regulating fluid flow and fluid level within a device for thermally ablating tissue, e.g., tissue lining an inner surface of a hollow organ. In particular, the present invention relates to devices for ablating the endometrium. However, those skilled in the art will understand that the present invention, and/or components thereof, may be utilized in conjunction with devices for prostate treatment (microwave or cyroablation), irrigation systems or other devices for procedures which infuse heated fluids to the body.

Fluid ablation systems generally utilize one or more resistive heating elements to warm a circulating fluid (e.g., saline) to a predetermined, substantially constant temperature. For example, such a thermal ablation system may heat the ablation fluid within a disposable cassette portion which is removably coupled to a reusable console. The heated ablation fluid may then be circulated through a hollow organ to ablate the lining thereof and returned to the system either for recirculation or disposal. One such system is described in a U.S. patent application entitled "Thermal Ablation System", naming as inventors Robert J. Bouthillier, Michael P. Fusaro, Joseph M. Gordon, Stephen S. Keaney, Brian MacLean, Andrew W. Marsella, David Robson and Boris Shapeton filed on Nov. 14, 2007 and assigned Ser. No. 60/987,913. The entire disclosure of this application is hereby expressly incorporated by reference herein. Those skilled in the art will understand that, although the precise temperature requirements for the ablation fluid may vary according to the type of procedure being performed, these systems are generally required to maintain this temperature within a narrow range for the entirety of the procedure to avoid complications such as burns where the temperature is excessive or a failure to sufficiently ablate the target tissue where the fluid temperature falls below the desired temperature range. The heating element may, for example, be powered by an alternating current ("AC") power source under control of a closed loop microprocessor based Proportional, Integral and Derivative ("PID") control. For example, a uterine ablation procedure requiring an ablation temperature of 90°±3° Celsius and more preferably 90°±2°, may require an AC power of 500 watts and a constant circulating fluid flow of about 200-300 ml/min.

The fluid follows a path passing a heating element which elevates the fluid temperature to the desired level, after which the fluid sweeps past thermistors, which detect the temperature of the fluid and transmit it to the PID. The fluid is then circulated through the hollow organ after which it is filtered and returned to the heating element for recirculation to the organ in a closed loop. A disruption of flow may cause fluid to collect by the heating element where it will be heated persistently, potentially elevating the temperature outside the allowable range. Devices according to the present invention identify when this situation has arisen and prevent fluid that has been excessively heated from flowing back to the body.

Those skilled in the art will understand that varying amounts of energy may be required during initial heating as well as during the ablation process to maintain the desired temperature. The main factors affecting the energy required to maintain a desired fluid temperature are fluid flow rate and heat loss to the patient and surroundings. Those skilled in the art will understand that the precise amount of required energy is also affected to a lesser degree by additional factors including ambient temperature conditions, the age and body fat index of the patient, humidity, heat absorption by the tissue, etc. Accordingly, the thermal ablation system must constantly compensate for the heat loss and activate or deactivate the heating system accordingly. In addition, the thermal ablation system must react to changes in fluid flow rate (e.g., to obstruction) as the average amount of energy required to maintain the temperature of a static volume of water decreases significantly. Since the fluid is no longer flowing to the treatment area where it loses heat, additional heating results in an increased temperature thereof. Current thermal ablation systems are designed to generate target flow levels but blockages, tubing kinks, pump malfunctions, etc. may frustrate this purpose.

A device according to an exemplary embodiment of the present invention enhances the ability of thermal ablation systems to address these concerns by generating an alert when such a flow occlusion is detected. The present invention employs a system measuring the average heater power required to maintain the desired temperature over time and, based on this power data, determines a rate of fluid flow through the heating chamber. Changes in the rate of flow through the heating chamber may then be used to detect problems with flow.

According to the exemplary embodiment, a software based PID algorithm controls the heating of the ablation fluid to a nominal set temperature. However, those skilled in the art will understand that any suitable algorithm, such as a PWM, an ON/OFF control, etc, may be employed to control the heating of the fluid and obtain the same results described herein. The PID algorithm adjusts power to the heating element by calculating a delay from the zero crossing of each AC cycle half wave before allowing any current to flow therethrough. As the delay period increases, the average current driven into the heating element decreases. Since this type of control is inherently non-linear (i.e., the size of the AC instantaneous voltage varies with delay), the PID compensates for the delay value so that the PID can linearly adjust power from zero to full-scale, as shown with respect to FIG. 1. As the amount of heat required to bring the fluid up to the desired temperature increases, the on time of the phase control signal also increases proportionally, in the direction A (i.e., the pulses grow increasingly wide while the gaps between pulses narrow). Those skilled in the art will understand that the particular method by which the PID alters the power does not impact operation of the system according to the present invention. For example, a system might maintain the size of the pulse by various means, such as controlling a percentage of full or half wave AC cycles in a given period of a PWM or simply controlling the on or off times to maintain a threshold around a setpoint temperature. In an alternate embodiment, an adjustable current source could be used to regulate the produced heat.

Figure 2:
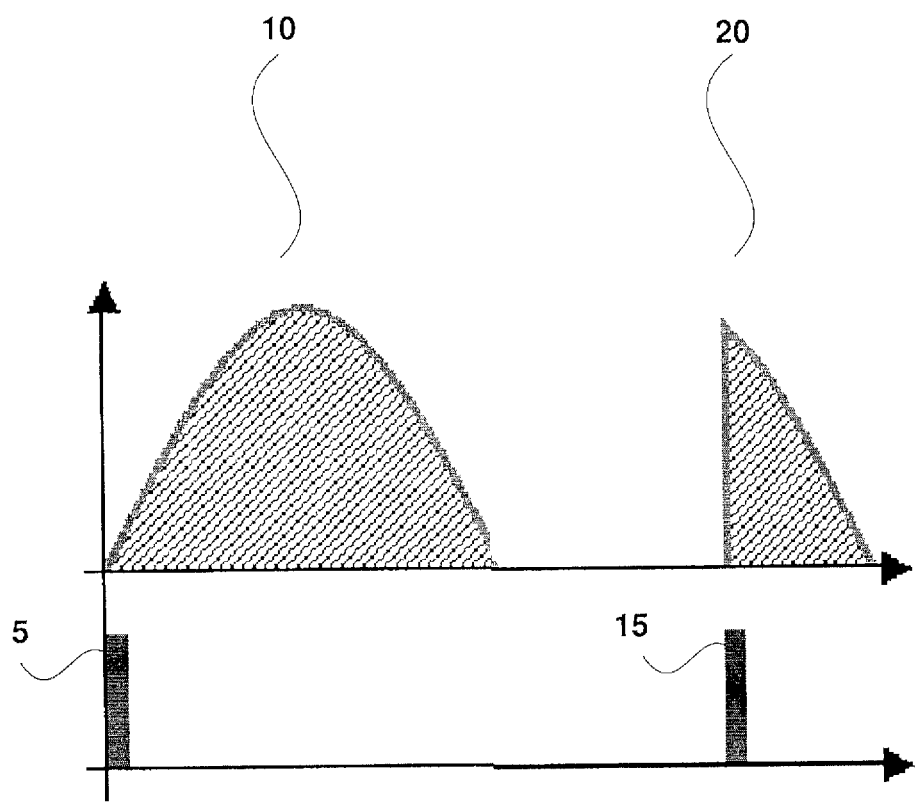
FIG. 2 shows phase control signals according to an exemplary embodiment of the present invention.

As further detailed with respect to FIG. 2, the phase control signal may modulate a waveform 10 or 20 in response to an on pulse 5, 15 or an off pulse received from a controller. For example, the waveform 10 is modulated in response to the on pulse 5, wherein the timing of the received on pulse 5 allows one half cycle of the waveform to be modulated. The off pulse is indicated by the termination of the waveform 10. The waveform 20, on the other hand, is modulated in response to an on pulse 15, wherein the timing of the pulse 15 allows for less than half of one wave cycle to be modulated. Those skilled in the art will understand that the phase control allows a solid state relay to turn on an adjustable amount of time after a zero crossing of the AC power wave, resulting in signals that are produced at varying stages of the AC power wave.

When the detected fluid temperature exceeds the setpoint, the PID algorithm reduces heat supplied to the system and conversely, when the temperature is below the setpoint, the PID algorithm increases heat supplied to the system. Varying temperature requirements from the heat control cause the PID to fluctuate from condition 1, when the maximum heat is generated, to condition 5 in which no heat is generated and though any of the intermediate conditions 2-4.

Those skilled in the art will understand that, when the temperature persists at a value greater than the setpoint, the PID may call for a negative heating value (i.e., cooling). In systems without an active cooling arrangement, this condition is equivalent to the heat off condition. As would be understood by those skilled in the art, systems that do not have active cooling are dependent on the natural heat loss characteristics of the system to lower temperature and are therefore generally slower in response than systems including an active cooling system.

The PID algorithm keeps track of the percentage of full scale heat the system is currently supplying via the heater element. Since the phase control is not linear in heat produced with phase delay, the PID uses a look up table to linearize the output so that heat can be linearly applied between zero and full scale.

The following exemplary code is one example of a suitable control logic for the PID algorithm.

```
if( s__bTestFlowFault && !g__bInhibitFlowFault )
    {
        if( GetPcntFS( ) <= 0 &&
        ( ( g__cTemp1Rate >=
        -2 && (g__iTempC1x10 >= (HIGH__TEMP__LIMIT/10L))) ||
        g__iTempC1x10 > (10+HIGH__TEMP__LIMIT/10L)))
            {
                if( s__ulLocalTime > (s__ulLowFlowTime +
                OCCLUSION__TIMEOUT ) )
                    {
                        s__ucNextPhase = s__Ph->ucLowFlowNextPhase;
                        g__ucExitCode = LOW__FLOW;
                        break;
                    }
            }
    else if( GetPcntFS( ) < 5 )
        {
            if( s__ulLocalTime > (s__ulLowFlowTime +
            (3*OCCLUSION__TIMEOUT)))
                {
                    s__ucNextPhase = s__Ph->ucLowFlowNextPhase ;
                    g__ucExitCode = LOW__FLOW;
                    break;
                }
        }
    else
        {
            s__ulLowFlowTime = s__ulLocalTime ;
        }
}
```

The above exemplary embodiment references the variables noted below. Those skilled in the art will understand that the noted values are exemplary only, specific to a standard uterine ablation procedure and that these values may be altered according to the requirements of the procedure to be performed.

GetPcntFS( ) returns the required Percentage of full scale heat ("% FS") to heat the fluid to a nominal temperature and may hold a value from −100% to 100%.

g__iTempC×10 is the temperature in tenths of a degree Celsius (i.e., 90° C. is 900). This value is obtained via sensors (e.g., the thermistors) in the thermal ablation device, which are connected to the PID.

g__iTemp1Rate corresponds to the temperature rate of change in tenths of a degree Celsius/second.

HIGH_TEMP_LIMIT corresponds to the user-defined limit of the maximum temperature of the ablation fluid. For example, an upper limit of 90° C. would equate to a value of 900.

OCCLUSION_TIMEOUT is defined as 5.0 seconds.

It is to be noted that the employment of the PID algorithm may constitute defining threshold values as described below which, when exceeded, indicate undesirable flow values. In reference to the above C code, the PID algorithm may perform the functions as noted below.

If the PID (1) calls for no heat, (2) indicates a temperature rate of change greater than a first threshold and (3) indicates that the temperature is above a second threshold and that this condition has persisted for a first predetermined time, a no flow condition may be declared, where the first threshold refers to rate of increase of fluid temperature and the second threshold refers to a first maximum temperature. Consequently, when these conditions are met, a user interface of the thermal ablation system may notify a clinician that fluid flow is obstructed. The notification may be carried out in any of a variety of manners (i.e., audible message, visual message on display screen of thermal ablation device, etc.). Additionally, the thermal ablation device may respond to the no flow declaration by automatically suspending the supply of heated fluid to the patient (i.e., by temporarily sealing the delivery lumen of the thermal ablation device, etc.) or by initiating any desired safety procedures relevant to this condition.

Additionally, if the temperature of the fluid, as read by the thermistors, is above a higher third threshold for a second predetermined time period, which may or may not be substantially equal to the first predetermined time, a no flow condition may be declared regardless of the other conditions. In this situation, the heat called for, temperature rate of change, etc. may be disregarded and a no flow condition declared. The third threshold refers to a second maximum temperature level allowable for the procedure, taking into account the allowable temperature deviation, which may vary in accordance with the procedure being performed, as mentioned earlier. If either of the above noted threshold conditions persists for a predetermined period of time, typically 5.0 seconds, the no flow condition will be declared.

In a second test, when the required Percentage of FS ("% FS") is below a particular predetermined value continuously for a second predetermined time (e.g., a period of time significantly longer than the first predetermined time), a no flow condition may be declared. For example, the second predetermined time may typically be 15 seconds. The % FS is indicative of the PID calling for little or no heat or, alternatively, for cooling (negative values). The second test may, for example, entail a situation where a procedure has been resumed without correcting a previously indicated flow problem. In this case, no further temperature rise may be expected since the PID has already throttled down the % FS heat.

The above detailed code may be implemented in a thermal ablation device in order to control and monitor the temperature and flow of fluid through the device. Those skilled in the art will understand that the described exemplary embodiments of the present invention may be altered without departing from the spirit or scope of the invention. Thus, it is to be understood that these embodiments have been described in an exemplary manner and are not intended to limit the scope of the invention which is intended to cover all modifications and variations of this invention that come within the scope of the appended claims and their equivalents.

What is claimed is:

1. A system for thermal ablation, comprising:
a heating element heating an ablation fluid flowing through an ablation device and to a target region of a body; and
a computing arrangement controlling power supplied to the heating element supplying power to heat the ablation fluid to a desired temperature, the computing arrangement reducing the supplied power when a detected ablation fluid temperature exceeds a desired temperature and increases the supplied power when the detected ablation fluid temperature is below the desired temperature, wherein the computing arrangement monitors a percentage of heat supplied by the heating element to heat the fluid to the desired temperature as a function of a maximum amount of heat which the heating element is capable of supplying.

2. The system of claim 1, further comprising a thermistor coupled to the computing arrangement to detect the temperature of the ablation fluid.

3. The system of claim 1, further comprising a cooling element, wherein when the computing arrangement determines that the detected ablation fluid temperature exceeds the desired temperature for a predetermined period of time, the computing arrangement provides power to the cooling element.

4. The system of claim 1, wherein when the percentage of heat holds a value from −100% to +100%.

5. The system of claim 1, wherein the power supplied by the heating arrangement is provided with a phase delay.

6. The system of claim 1, wherein if the percentage of heat supplied by the heating element falls below a predetermined value for a predetermined period of time, a no-flow condition is declared.

7. The system of claim 6, wherein the computing arrangement is configured to one of reduce and terminate power to the heating element when the no-flow condition is declared.

8. The system of claim 1, wherein the computing arrangement supplies power to the heating element using one of a variable phase angle control, a pulse width modulated control and an on/off control.

9. The system of claim 6, wherein the computing arrangement is configured to provide a notification when the no-flow condition is detected.

10. The system of claim 9, wherein the notification is one or more of an audible message and a visual message.

11. The system of claim 6, wherein the computing arrangement is configured to seal a lumen of the ablation device when the no-flow condition is detected.

12. A method of ablating tissue, comprising:
controlling a heating element to supply heat to an ablation device using a PID algorithm, the ablation device providing a flow of ablation fluid therethrough and into a target region of a body;
regulating a temperature of fluid through the ablation device and into a target ablation region by controlling power supplied by a computing arrangement to the heating element based on an algorithm configured to supply power to heat the ablation fluid to a desired temperature, the algorithm configured to reduce supplied power when detected ablation fluid temperature exceeds the desired temperature and increase supplied power supplied when the detected ablation fluid temperature is below the desired temperature;
monitoring a percentage of heat supplied by the heating element as a function of a maximum amount of heat which the heating element is capable of supplying; and
executing a safety procedure if the detected ablation fluid temperature exceeds a predetermined temperature for a predetermined period of time.

13. The method of claim 12, wherein the safety procedure includes sealing a lumen of the ablation device to prevent flow into the target region.

14. The method of claim 12, wherein the safety procedure includes supplying power to a cooling element.

15. The method of claim 12, wherein the safety procedure includes reducing power to the heating element based on the PID algorithm.

16. The method of claim 15, wherein the safety procedure including temporarily eliminating power to the heating element.

17. The method of claim 12, wherein the safety procedure includes providing feedback to a user indicating a no-flow condition, the feedback being one or both of a visual signal and an audible signal.

18. The method of claim 12, further comprising the step of monitoring a percentage of heat supplied by the heating arrangement as a function of a maximum total the heating element is capable of applying.

19. A system for ablating tissue, comprising:
   a heating element heating an ablation fluid circulating through an ablation device and a target region of a body;
   a computing arrangement controlling power supplied to the heating element based on an algorithm configured to supply power to heat the ablation fluid to a desired temperature, the algorithm configured to reduce the supplied power when detected ablation fluid temperature exceeds the desired temperature and increase the supplied power when the detected ablation fluid temperature is below the desired temperature wherein the computing arrangement monitors a percentage of heat supplied by the heating element to heat the fluid to the desired temperature as a function of a maximum amount of heat which the heating element is capable of supplying; and
   a thermistor coupled to the computing arrangement to detect the temperature of the ablation fluid.

* * * * *